United States Patent [19]

Cornelius

[11] 4,348,482
[45] Sep. 7, 1982

[54] PROCESS FOR DECREASING THE THERMAL STABILITY OF MICROBIAL RENNET

[75] Inventor: Dennis A. Cornelius, Elkhart, Ind.

[73] Assignee: Miles Laboratories, Inc., Elkhart, Ind.

[21] Appl. No.: 73,647

[22] Filed: Sep. 10, 1979

Related U.S. Application Data

[63] Continuation-in-part of Ser. No. 908,575, May 22, 1978, abandoned.

[51] Int. Cl.$^3$ ...................... C12N 9/58; A23C 19/032
[52] U.S. Cl. ..................................... 435/223; 426/36; 426/63; 435/931
[58] Field of Search ................ 426/36, 63, 522, 330.2; 435/223, 800, 184, 931

[56] References Cited

U.S. PATENT DOCUMENTS

| | | | |
|---|---|---|---|
| 2,053,740 | 9/1936 | Reichert et al. | 426/330.2 |
| 2,125,398 | 8/1938 | Reichert et al. | 425/330.2 |
| 3,886,288 | 5/1975 | Rice et al. | 426/36 |
| 4,136,201 | 1/1979 | Feldman | 426/36 |
| 4,255,454 | 3/1981 | Branner-Jorgensen | 426/36 |

OTHER PUBLICATIONS

Ilany et al., Milk–Clotting Activity of Proteolytic Enzymes, J. Da. Sci., vol. 52, No. 1, 1969 (pp. 43–46).
Neumann, N. P., Oxidation with Hydrogen Peroxide, Methods in Enzymology, vol. XXV, 1972 (pp. 393–400).
Regmier, J. M., Thermal Resistance of Clotting Enzymes, Chemical Abstracts, vol. 87: 518172, 1977 (p. 352).
Iori et al., Dye–Sensitized Selective Photooxidation of Methionine, Biochemica et Biophysica ACTA, vol. 154, 1968 (pp. 1–9).
McBride-Warren et al., Structural and Functional Determinants of Mucor Miehei Protease, Biochimica et Biophysics ACTA, vol. 328, 1973 (pp. 52–60).

*Primary Examiner*—David M. Naff
*Attorney, Agent, or Firm*—Louis E. Davidson

[57] ABSTRACT

A process is provided for decreasing the thermal stability of Mucor microbial rennet without substantially reducing its milk-clotting activity by contacting an aqueous solution thereof with a methionine-oxidizing means under conditions effective substantially to decrease the thermal stability of the microbial rennet. The resultant treated microbial rennet is dramatically less heat stable than untreated microbial rennet and can serve as replacement for calf rennet in traditional cheese-making processes. The preferred methionine-oxidizing means is hydrogen peroxide or dye-sensitized photooxidation.

18 Claims, No Drawings

PROCESS FOR DECREASING THE THERMAL STABILITY OF MICROBIAL RENNET

CROSS REFERENCE TO RELATED APPLICATION

This application is a continuation-in-part application of U.S. Ser. No. 908,575 filed May 22, 1978 now abandoned.

BACKGROUND AND PRIOR ART

For centuries, calf rennet has been used as a milk coagulant in the production of all varieties of cheese. In face, cheeses made with this enzyme set the standards for flavor, appearance and texture with which cheeses made from other coagulants are compared. Recently, dramatic increases in world cheese production and decreases in calf rennet supplies have stimulated the use of alternative milk coagulant enzymes.

Among the available enzymes for this purpose, the microbial rennets are favored because they can be mass produced and offer a variety of properties permitting selection of those most suitable in cheese production. Unfortunately, the increased thermal stability, especially when compared to calf rennet, of microbial rennets, such as the Mucor microbial rennets, has been considered to be a less desirable property of these enzymes.

In the cheese-making process, the whey that separates from the rennet-coagulated curd is collected as a valuable source of whey proteins. Normally, the collected whey is pasteurized, at a temperature from about 60° C. to 71° C., for a sufficient time to destroy any microorganisms and to thermally inactivate at least about 80 to 90% of any residual rennet coagulant. Residual levels of coagulant enzyme retaining much more than about 20% of their original milk-clotting activities after normal pasteurization have been found to undesirably hydrolyze the valuable whey proteins and restrict the use of the whey as an ingredient in various food products. The normal pasteurizing conditions, which are sufficiently mild to leave the whey proteins unaffected but sufficiently severe to thermally inactivate calf rennet, are much less effective to inactivate microbial rennet coagulants to the desired level. This problem is further complicated by the fact that more microbial rennet is partitioned into the whey than is calf rennet. As a result there has been a continuing effort to improve the thermal lability of microbial rennet.

Several microbiological approaches to obtain more heat-labile microbial coagulants have been tried. These approaches include comprehensive screens for new microorganisms and mutations of known rennet-producing microorganisms. To date, neither approach has been successful in obtaining an acceptable microbial coagulant with the desired thermal properties.

Chemical approaches to modify various properties of enzymes have also been tried but, in general, are severely limited by a concomitant loss in the enzyme's milk-clotting activity. Recent studies, however, to determine the structural and functional determinants of one Mucor microbial rennet indicate that some chemical modification of microbial rennet may not result in the total loss of milk coagulant activity. Such modifications include nitration (Biochemica et Biophysica Acta, 371, 368 [1974]), carbamylation (ibid., 271, 93 [1972] and periodate-induced deglycosylation (ibid., 328, 52 [1973]) of the glycoenzyme from Mucor microbial rennet. Of these modifications, there is some suggestion that carbamylation and periodate-induced deglycosylation may impart some increased thermal lability. Unfortunately, these chemical approaches have not been completely successful in producing a microbial rennet with the desired degree of thermal lability.

It is therefore highly desirable to produce a microbial rennet with desirable milk coagulant properties but with substantially increased thermal labile properties.

SUMMARY OF THE INVENTION

In accordance with the present invention, a process is provided for decreasing the thermal stability of Mucor microbial rennet by contacting an aqueous solution thereof with methionine-oxidizing means under conditions effective substantially to decrease the thermal stability of the microbial rennet.

DESCRIPTION OF THE INVENTION

The thermally stable microbial rennets that are most effectively treated by this process are prepared from Mucor microorganisms by well-known procedures and are commercially available in aqueous solution. Such rennets include those produced from *Mucor miehei, Mucor pusillus* and the like. The native coagulant enzymes from these sources are known to be more heat stable than calf rennet. This process may be applied to pure, partially pure or even very crude fermentation liquors of the microbial rennet.

Methionine-oxidizing means are well-known and include the use of hydrogen peroxide, dye-sensitized photooxidation and the like that are able to oxidize at least a portion of the methionine residues in the microbial rennet to methionine sulfoxide. The use of such methionine-oxidizing means has been found effective substantially to decrease the heat stability of the microbial rennet, Hydrogen peroxide is the preferred methionine-oxidizing means.

The hydrogen peroxide used in this invention is commercially available or can be produced in situ by familiar means. For example, inorganic and organic peroxides are known to produce hydrogen peroxide on contact with water. Any suitable hydrogen peroxide-producing means which does not severely inactivate the microbial rennet prior to thermal treatment may be selected, including the use of sodium peroxide, calcium peroxide, benzoyl hydroperoxide, a mixture of cumene hydroperoxide and peroxidase, urea hydrogen peroxide and the like. The inorganic peroxides are preferred.

Dye-sensitized photooxidation is well-known (see Industrial and Engineering Chemistry, 55, 40 [1963]) and is described in Biochemica et Biophysica Acta, 154 1 (1968) as a selective means for oxidizing methionine residues in such substrates as ribonuclease A and various peptides as well as the free amino acid. Such photooxidation of ribonuclease A, however, results in a substantial loss (52–82%) of activity. Surprisingly, it has now been found that the photooxidation of microbial rennet does not result in substantial loss of enzyme activity prior to thermal treatment but does substantially decrease the thermal stability of the microbial rennet. Such photooxidation is accomplished by contacting an aqueous solution of the microbial rennet with oxygen in the presence of light and a photosensitizer. The light source can be provided by sunlight, incandescent light, fluorescent light, ultraviolet light and the like. Oxygen either alone or in admixture with other gases, such as air, can be used. Photosensitizers include methylene blue, rose bengal, oxidation-reduction indicators, mixtures thereof and the like.

In the practice of this invention, an aqueous solution of the thermally stable microbial rennet mentioned above is contacted with the methionine-oxidizing means under conditions effective substantially to decrease its thermal stability (i.e. increase thermal lability), preferably to achieve a residual milk-clotting activity after thermal treatment at least below about 20 percent of its original milk-clotting activity before thermal treatment, and most preferably to at least about the thermal stability of calf rennet. The thus-treated solution of microbial rennet can be used as is, concentrated or further purified as may be required by the particular cheese-making process.

Those skilled in the art will appreciate that the above process can be practiced as a batch or continuous process and that the conditions of contact with the methionine-oxidizing means, i.e. concentration of materials, pH, temperature and contact time, will vary widely depending upon the thermal stability of the native microbial rennet, the type of process and the equipment selected. Such conditions, however, should be selected which do not severely affect the original milk-clotting activity of the microbial rennet prior to thermal treatment.

The concentration of microbial rennet in the aqueous solution is most conveniently expressed in terms of milk-clotting enzymatic activity, i.e. Soxhlet Units (SU) per ml, as determined by the procedure described in J. of Dairy Science, Vol. 54, No. 2, 159–167 (1971) which is incorporated herein by reference. The milk-clotting activity is determined on a 10% weight/volume basis (W/V) solution of milk solids containing 0.01 M $CaCl_2$ at pH 6.45 to 6.50. Five milliliters of milk are incubated at 37° C. ±0.5 with 0.5 ml of enzyme solution. The time necessary for the appearance of the milk clot is measured. One Soxhlet Unit is defined as that enzyme activity which clots one (1) ml of a milk substrate in 40 minutes under the conditions of the assay procedure. In practice, the milk-clotting activity of the aqueous solution of microbial rennet will preferably vary from about 5,000 SU/ml to about 100,000 SU/ml.

When hydrogen peroxide is the selected methionine-oxidizing means, the amounts of hydrogen peroxide used to treat the aqueous solution of microbial rennet will depend upon the enzyme's activity, original heat stability and purity. The concentration of hydrogen peroxide in the aqueous solution varies between about 1% and 25% hydrogen peroxide on a volume/volume (V/V) basis based on the original volume of the aqueous solution. Preferably, the amount is between 2% and 10% (V/V) based on the original volume. At concentration much above about 25% (V/V), the benefit becomes asymptotic, and at concentrations much below about 1% (V/V), the reaction rate becomes unduly long.

When dye-sensitized photooxidation is the selected methionine-oxidizing means, the photosensitizers behave somewhat like catalysts without undergoing any permanent change. Thus, concentration of the photosensitizer can be varied widely. The upper limit of concentration is dependent upon the solubility of the photosensitizer in the aqueous system. The lower limit of concentration should be sufficient to merely initiate the photooxidation; for example, a concentration of from about 0.0025 mM to about 1.0 mM of the photosensitizers has been used successfully. Preferably, the concentration is from about 0.025 mM to about 0.1 mM.

The temperature used to treat the microbial rennet varies between about 4° C. and 30° C. Preferably, the temperature is between about 4° C. and 20° C. At temperatures much above 30° C. the enzyme undesirably loses activity, and at temperatures much below about 4° C. the reaction rates become unduly long.

The pH for the treatment will preferably range between about pH 3.0 and 8.0. At pH values much above about pH 8.0, the enzyme is undesirably inactivated, and at pH values much below pH 3.0 the solubility and the activity of the enzyme diminish and the reaction time increases.

The contact time is a function of the particular contact conditions selected but should be sufficient to substantially decrease the microbial rennet's thermal stability to a desired level. Under the preferred conditions, contact times between about 15 minutes and 72 hours have been used most successfully.

In a preferred mode of this invention using hydrogen peroxide as the methionine-oxidizing agent, the hydrogen peroxide-treated solution is further treated to substantially destroy any residual or excess hydrogen peroxide in the solution using any convenient means which does not inactivate the microbial rennet. Residual hydrogen peroxide may be destroyed with the use of a material selected from the group consisting of catalase, such as beef liver catalase, peroxidase, such as horseradish peroxidase, ascorbic acid and the like. These hydrogen peroxide-destroying means can be effectively used under the prevailing conditions used for the hydrogen peroxide treatment. In practice, the amount of hydrogen peroxide remaining in the solution after treatment is determined by any convenient detection means as is well known in the cheese industry, such as addition of sodium iodide and back titration of the liberated iodine with thiosulfate. A suitable amount of the hydrogen peroxide-destroying means is then added to the microbial rennet solution, and residual amounts of the hydrogen peroxide are monitored with the detection means until the hydrogen peroxide is substantially destroyed. Beef liver catalase is a preferred means and is effective to substantially decrease the hydrogen peroxide to the desired level under the preferred conditions above in a period from about 1 to 3 hours.

When dye-sensitized photooxidation is selected as the methionine-oxidizing means, it is preferred to remove any residual or excess amounts of the photosensitizer using any convenient means which does not inactivate the microbial rennet. For example, photosensitizers, such as methylene blue and rose bengal, can be easily removed from the treated rennet solution by solvent extraction, dialysis and the like. Photosensitizers bound to solid supports, such as ion exchange resins, are known. If such bound photosensitizer is used, it can be removed from the microbial rennet by merely physically separating the support from the solution.

The thermal stability of the thus-treated microbial rennet is determined under conditions which are normally used to pasteurize cheese whey solutions. The following model is useful in reproducing these pasteurization conditions. A one (1) ml aliquot of the rennet-containing solution is diluted to 100 ml with a sodium phosphate buffer (pH 5.5). Aliquots (2 to 3 ml) of this diluted solution are then placed in sealed glass tubes and heated in a water bath to a temperature from 60° C. to 71° C. for periods of time from 0 to 20 minutes. The heated samples are cooled and then assayed for their milk-clotting activities. Under these model pasteurization conditions, the residual activity of the rennet found in cheese whey is decreased after the thermal treatment to a desired residual milk-clotting activity level, preferably at least below about 20 percent of the original milk-clotting activity before the thermal treatment. Using the preferred conditions of this invention, the treated enzymes, especially the hydrogen peroxide-treated microbial rennets, are found to be as thermally labile as calf rennet when subjected to the same thermal conditions.

The microbial rennet produced according to this process is useful in all traditional cheese-making processes that now use microbial rennet as a milk coagulant. Since the novel treated microbial rennet is dramatically less thermally stable than the untreated microbial rennet, it can serve as a reasonable replacement for calf rennet. Used in these cheese-making processes, the treated microbial rennet of this invention is desirably inactivated by the normal conditions used to pasteurize the cheese whey, and the resulting whey can be fully utilized for its valuable whey protein.

The following examples are illustrative of the inventive concept but are not intended to limit the scope thereof.

EXAMPLE 1

This example illustrates a typical treatment of various Mucor microbial rennets using hydrogen peroxide as a methionine-oxidizing means.

Aqueous fermentation broths of microbial rennet from *Mucor miehei* (pH 4.5) containing 49,800 SU/ml and *Mucor pusillus* (pH 5.5) containing 49,800 SU/ml were obtained from commercial sources. Samples (1000 ml) of the aqueous broths were cooled to 4° C., and the pH of each was adjusted to pH 7.0 by the addition of 20% (W/V) aqueous sodium hydroxide. To each sample there were then added 100 ml of 30% (V/V) hydrogen peroxide (Analytical Reagent grade). This corresponds to a concentration of about 3% (V/V) hydrogen peroxide based on the original volume of the aqueous broth. These samples were allowed to stand for 24 hours at 4° C. in contact with the hydrogen peroxide. Beef liver catalase [0.3 ml, 100 Keil Units (KU) per 1 ml; 1 KU decomposes 1.0 g of $H_2O_2$/10 min. at 25° C. at pH 7.0] was then added to the solutions to destroy any excess hydrogen peroxide, and the mixtures were allowed to stand (about 2 to 3 hours) at room temperature until negative peroxide tests were obtained. The solutions were back adjusted to their original pH values with 12 N HCl and concentrated to their original volume of 1000 ml by flash evaporation.

The milk-clotting activity of the microbial rennet was determined on 10% (W/V) solutions of milk solids containing 0.01 M $CaCl_2$ adjusted to about pH 6.5 with lactic acid. Five ml of milk were incubated at 37° C. with 0.5 ml of sample of the enzyme solution. The time necessary for the appearance of the clot was measured. Enzyme activity was expressed in terms of Soxhlet clotting units (SU). The hydrogen peroxide treatment of *Mucor miehei* microbial rennet resulted in the total retention of milk-clotting activity while the hydrogen peroxide treatment of *Mucor pusillus* microbial rennet resulted in the retention of 80 to 90% of the milk-clotting activity.

To determine the thermal stability of the hydrogen peroxide-treated enzymes, aliquots (1 ml) of the native and treated rennets were diluted to 100 ml with 0.2 M sodium phosphate buffer (pH 5.5). Aliquots (2 ml) of these diluted solutions were placed in screw top test tubes and heated in a water bath at 60° to 70° C. for various times. After the heat treatment, the samples were cooled by immersion in an ice-water bath and were assayed for their residual milk-clotting (MC) activities by the method described above. The results of these studies are given in Table A below.

TABLE A

| Sample | Pasteurization Conditions | | % Residual MC Activity After Pasteurization |
|---|---|---|---|
| | T° C. | Time(Min) | |
| M. pusillus (native) | 60 | 0 | 100 |
| | | 4 | 95 |
| | | 8 | 90 |
| | | 12 | 89 |
| | | 16 | 87 |
| | | 20 | 82 |
| M. pusillus ($H_2O_2$ treated) | 60 | 0 | 100 |
| | | 4 | 34 |
| | | 8 | 18 |
| | | 12 | 11 |
| | | 16 | 6.9 |
| | | 20 | 0 |
| M. miehei (native) | 70 | 0 | 100 |
| | | 4 | 94 |
| | | 8 | 79 |
| | | 12 | 72 |
| | | 16 | 66 |
| | | 20 | 61 |
| M. miehei ($H_2O_2$ treated) | 70 | 0 | 100 |
| | | 4 | 19 |
| | | 8 | 5.2 |
| | | 12 | 2.0 |
| | | 16 | 0 |
| | | 20 | 0 |

The above data clearly illustrate that the hydrogen peroxide treatment is effective to dramatically reduce the heat stability of the enzymes as expressed in terms of their milk-clotting activity and as compared with the native (untreated) enzymes.

Samples of the native (untreated) *Mucor miehei* microbial rennet and the hydrogen peroxide-treated rennet similarly prepared as described above were extensively purified using the following purification procedure which is described in J. of Dairy Science, 54, 159–167 (1971). The samples were precipitated with ammonium sulfate, dissolved in water, dialyzed against tap water and lyophilized. The lyophilized samples were then separated on a column of Amberlite CG50 ion-exchange resin using 0.1 N sodium acetate buffer (pH 4.75) for elution and the desired elution fractions containing the most enzyme activity were pooled and concentrated by ultrafiltration. The concentrated samples were then chromatographically separated on a column of carboxymethyl cellulose using 0.1 M sodium acetate buffer solutions (pH 3.6 followed by pH 4.5) for elution, and the desired elution fractions were collected and concentrated by ultrafiltration. The resultant samples were then subjected to gradient elution on a column of carboxymethyl cellulose using linear gradients prepared from 0.1 M sodium acetate (pH 3.6) and 0.1 M sodium acetate (pH 4.8). The desired elution fractions were collected, dialyzed against water and lyophilized.

The purified samples of the above native and hydrogen peroxide-treated enzyme were then subjected to alkaline hydrolysis. Eleven (11) milligrams of purified enzyme were dissolved in 1 ml of 4 N sodium hydroxide solution containing 25 mg of soluble starch as an antioxidant, sealed in evacuated vials and heated at 110° C. for 16 hours to hydrolyze the enzyme. After hydrolysis, the samples were cooled, diluted to 10 ml, and 20 μl were subjected to automatic amino acid analysis. Partial amino acid profiles are given in the following Table B.

TABLE B

| Amino Acid | Quantity (ng) | |
|---|---|---|
| | Native | Hydrogen Peroxide-Treated |
| Methionine Sulfoxide | 0 | 241.8 |
| Aspartic Acid | 2400.6 | 2169.3 |
| Threonine | 57.2 | 60.9 |
| Serine | 455.0 | 434.1 |
| Glutamic Acid | 1671.5 | 1530.8 |
| Proline | 888.7 | 802.0 |
| Glycine | 1807.0 | 1630.0 |
| Alanine | 1772.5 | 1534.6 |
| Valine | 503.0 | 514.5 |
| Methionine | 311.2 | 130.0 |

The above data illustrate that the hydrogen peroxide treatment was effective to oxidize the methionine residues to methionine sulfoxide.

EXAMPLE 2

This example illustrates the effects of pH on the milk-clotting activity and thermal stability of microbial rennet treated by this process using hydrogen peroxide as the methionine-oxidizing means.

Ten ml aliquots of an aqueous broth of microbial rennet from *Mucor miehei* (pH 4.5) containing 49,800 SU/ml were adjusted to various pH values between 4.5 and 7.5 using 20% (W/V) aqueous sodium hydroxide. Each sample was treated with 0.6 ml of 30% (V/V) hydrogen peroxide (corresponding to 1.8% (V/V) $H_2O_2$ based on the original volume). One untreated sample served as a control. All samples were stored at 4° C. for 24 hours and then treated with 5 ml of 20% (W/V) aqueous ascorbic acid (to decompose any $H_2O_2$) and stored at 4° C. for 48 hours. Each mixture was diluted a hundred fold with 0.2 M sodium phosphate buffer (pH 5.5). The milk-clotting (MC) activities were determined using the procedure described in Example 1. These results are given in Table C below.

TABLE C

| Treatment pH | % of Original MC Activity |
|---|---|
| 4.5 (control) | 100 |
| 4.5 | 94 |
| 5.1 | 89 |
| 5.8 | 92 |
| 6.3 | 94 |
| 6.9 | 97 |
| 7.5 | 100 |

The data in Table C clearly demonstrate that the instant process does not severely affect the milk-clotting activity of the treated microbial rennet even over the broad pH range from 4.5 to 7.5.

The thermal stability of the treated microbial rennet was determined using the pasteurization procedure described in Example 1. The milk-clotting activities were measured after pasteurization and reported as a percentage of the original activity before pasteurization. The data are reported in Table D below.

TABLE D

| Treatment pH | Pasteurization Time Minutes at 70° C. | % Residual MC Activity |
|---|---|---|
| 4.5 (control) | 0 | 100 |
| | 4 | 93 |
| | 8 | 84 |
| | 12 | 72 |
| 4.5 | 0 | 100 |
| | 4 | 39 |
| | 8 | 12.4 |
| | 12 | 5.6 |
| 6.3 | 0 | 100 |
| | 4 | 37.6 |
| | 8 | 13 |
| | 12 | 4.4 |
| 7.5 | 0 | 100 |
| | 4 | 10.7 |
| | 8 | 2.6 |
| | 12 | 0 |

The data in Table D illustrate that the samples treated with hydrogen peroxide over the pH range from 4.5 to 7.5 are dramatically more heat labile than the untreated control.

EXAMPLE 3

This example illustrates the effects of contact time on the milk-clotting activity and thermal stability of microbial rennet treated by this process using hydrogen peroxide as the methionine-oxidizing means.

A 200 ml portion of an aqueous solution of *Mucor miehei* microbial rennet containing 49,800 SU/ml was adjusted to pH 7.0 with 20% (W/V) aqueous sodium hydroxide cooled to 4° C. and 20 ml of 30% (V/V) hydrogen peroxide was added to the solution to result in a 3% (V/V) concentration of $H_2O_2$ based on the original volume. This mixture was maintained at 4° C. for several days during which time aliquots (1 ml) were removed, then treated with beef liver catalase (0.01 ml, 100 KU/ml) and further diluted a hundred fold with 0.2 M sodium phosphate buffer (pH 5.5). The milk-clotting (MC) activities were determined using the procedure described in Example 1. These results are given in Table E below.

TABLE E

| Contact Time (Hours) | % of Original MC Activity |
|---|---|
| 0 | 100 |
| 17 | 103 |
| 26 | 108 |
| 41 | 105 |
| 50 | 113 |
| 65 | 101 |
| 73 | 113 |
| 136 | 111 |

The data in Table E demonstrate that this process does not adversely affect the milk-clotting activity of the treated microbial rennet even over extended contact times.

The thermal stability of each of several selected samples of the treated microbial rennet was determined using the pasteurization procedure described in Example 1. The milk-clotting (MC) activities were measured after pasteurization and reported as a percentage of the original MC activity in the sample before pasteurization. The data are reported in Table F below.

TABLE F

| Contact Time Hours | Pasteurization Time Minutes at 70° C. | % Residual MC Activity |
|---|---|---|
| 0 | 0 | 100 |
|   | 4 | 94 |
|   | 8 | 79 |
|   | 12 | 72 |
| 26 | 0 | 100 |
|   | 4 | 19 |
|   | 8 | 5.2 |
|   | 12 | 2 |
| 73 | 0 | 100 |
|   | 4 | 9.6 |
|   | 8 | 1.6 |
|   | 12 | 0 |
| 136 | 0 | 100 |
|   | 4 | 6.6 |
|   | 8 | 1.6 |
|   | 12 | 0 |

The data in Table F show that the samples treated with hydrogen peroxide over a broad range of contact times are dramatically more heat labile than an untreated control.

EXAMPLE 4

This example illustrates the effects of hydrogen peroxide concentration on the milk-clotting activity and thermal stability of microbial rennet treated by this process.

A 250 ml portion of an aqueous solution of *Mucor miehei* microbial rennet containing 99,600 SU/ml was adjusted to pH 7.0 with 20% (W/V) aqueous sodium hydroxide. Ten ml aliquots were removed and various amounts of hydrogen peroxide (30% V/V) were added to give solutions ranging from 3% (V/V) to 9% (V/V) $H_2O_2$ based on the original volume. Each sample was then stored at 4° C. for 77 hours. Sufficient beef liver catalase was added (0.1 ml, 100 KU/ml) to destroy the hydrogen peroxide in the sample. Each sample was then diluted a hundred fold with 0.2 M phosphate buffer (pH 5.5). The milk-clotting (MC) activities were determined using the procedure described in Example 1. These results are reported in Table G below.

TABLE G

| $H_2O_2$ Concentration % V/V | % of Original MC Activity |
|---|---|
| 0 | 100 |
| 3.0 | 91 |
| 4.2 | 91 |
| 5.4 | 96 |
| 6.0 | 97 |
| 7.2 | 97 |
| 8.4 | 93 |
| 9.0 | 93 |

The data in Table G show that this process does not severely affect the milk-clotting activity of the treated microbial rennet even over a range of $H_2O_2$ concentrations.

The thermal stability of each of several selected treated samples was determined using the pasteurization procedure (at 65° C.) described in Example 1. The milk-clotting activities were measured after pasteurization and reported as a percentage of the original MC activity in the sample before pasteurization. The data are reported in Table H below.

TABLE H

| $H_2O_2$ Concentration % V/V | Pasteurization Time Minutes at 65° C. | % Residual Activity |
|---|---|---|
| 0 | 0 | 100 |
|   | 8 | 100 |
| 3 | 0 | 100 |
|   | 8 | 21 |
| 6 | 0 | 100 |
|   | 8 | 10 |
| 9 | 0 | 100 |
|   | 8 | 4 |

The data in Table H show that the samples treated with hydrogen peroxide over a range of $H_2O_2$ concentrations are dramatically more heat labile than an untreated control.

EXAMPLE 5

This example illustrates the use of hydrogen peroxide produced in situ on the thermal stability of microbial rennet treated by this process.

Purified microbial rennet (500 mg) from *Mucor miehei* was dissolved in 100 ml of 1.0 N sodium acetate buffer (pH 4.5). This aqueous solution of the enzyme contained about 9,960 SU/ml. A ten ml aliquot of this solution was removed and 500 mg of calcium peroxide was added thereto. This amount of calcium peroxide on contact with water present was sufficient to produce a calculated amount of hydrogen peroxide in situ equivalent to about 2.35% $H_2O_2$ (V/V) based on the original volume. The sample was stored at about 20° C. for about 15 to 18 hours at pH 4.5. To destroy any excess peroxide, beef liver catalase (0.1 ml; 100 KU/ml) was then added. The sample was diluted twenty fold with 0.2 M sodium phosphate buffer (pH 5.5), and the thermal stabilities of the treated sample and untreated control were determined using the pasteurization procedure (at 60° C.) described in Example 1. The milk-clotting (MC) activities were measured before and after pasteurization and values reported as a percentage of the original MC activity. The data are reported in Table I below.

TABLE I

| $CaO_2$ (mg) | % $H_2O_2$ (V/V) | Pasteurization Time (Min) at 60° C. | % Residual MC Activity |
|---|---|---|---|
| 0 | 0 | 0 | 100 |
|   |   | 8 | 97 |
|   |   | 16 | 97 |
|   |   | 20 | 94 |
| 500 | 2.35 | 0 | 100 |
|   |   | 8 | 37 |
|   |   | 16 | 23 |
|   |   | 20 | 21 |

The data in Table I clearly show that hydrogen peroxide produced in situ by this process is effective to dramatically reduce the thermal stability of the treated microbial rennet compared to the untreated control.

EXAMPLE 6

This example illustrates the use of the microbial rennet treated by this process to produce cheese.

Batches of cheddar cheese were prepared, using a conventional procedure, from 196 kg of pasteurized whole milk and 1% commercial starter culture. A control vat was coagulated with 22.5 ml of untreated *Mucor*

*miehei* microbial rennet containing about 93,000 SU/ml. A test vat was coagulated with 26.5 ml of *Mucor miehei* microbial rennet treated as described in Example 4 with 3% (V/V) hydrogen peroxide and which contained about 79,000 SU/ml. The respective times for milk clot formation were measured and were determined to be equivalent. After cheese manufacture, the whey liquids were collected, adjusted to pH 6.1 with sodium hydroxide and analyzed for residual enzyme activity before and after flash pasteurization. The enzyme activities are compared in Table J below as a percentage of the original MC activities in the whey.

TABLE J

| Sample | Pasteurization Conditions | % of Original MC Activity in Whey |
|---|---|---|
| Untreated Control | None | 100 |
|  | 63° C. for 20 sec. | 99 |
|  | 63° C. for 30 sec. | 100 |
| $H_2O_2$ Treated | None | 100 |
|  | 63° C. for 5 sec. | 30 |
|  | 63° C. for 10 sec. | 30 |
|  | 63° C. for 15 sec. | 26 |
|  | 63° C. for 20 sec. | 23 |

The cheeses prepared above were aged at 7° C. for 30 days and compared with one another by a trained sensory panel. The cheese made with $H_2O_2$ treated microbial rennet was well accepted and found to be desirably similar in flavor and texture to the cheese made with untreated native microbial rennet.

The above data clearly show that the $H_2O_2$ treated microbial rennet is as effective as the native microbial rennet to produce cheese but the $H_2O_2$ treated microbial rennet is much more heat labile than the native microbial rennet.

EXAMPLE 7

This example compares the heat stabilities of calf rennet and microbial rennet treated by this process.

*Mucor miehei* microbial rennet containing 99,600 SU/ml was treated with 3% (V/V) $H_2O_2$ as described in Example 4, and the thermal stability of the product was compared with the native microbial rennet before treatment and with calf rennet containing about 49,800 SU/ml using the pasteurization procedure (at 60° C.) described in Example 1. The milk-clotting (MC) activities were measured after pasteurization and reported as a percentage of the original MC activity in the sample before pasteurization. The data are reported in Table K below.

TABLE K

| Sample | Pasteurization Time Minutes at 60° C. | % Residual MC Activity |
|---|---|---|
| Microbial rennet (untreated) | 0 | 100 |
|  | 8 | 98 |
|  | 20 | 98 |
| Microbial rennet ($H_2O_2$ treated) | 0 | 100 |
|  | 8 | 60 |
|  | 20 | 38 |
| Calf Rennet | 0 | 100 |
|  | 8 | 72 |
|  | 20 | 55 |

The data in Table K clearly show that the instant process is effective to reduce the heat stability of microbial rennet to about the heat stability of calf rennet.

EXAMPLE 8

This example illustrates the treatment of Mucor microbial rennet using dye-sensitized photooxidation as the methionine-oxidizing means.

Two aqueous fermentation broths of microbial rennet from *Mucor miehei* (pH 4.85), coded MR-160 containing 76,680 SU/ml and MR-40 containing 19,920 SU/ml, were obtained from commercial sources. A 0.2 mM solution of methylene blue was prepared by dissolving 74.8 mg of the dye in 1000 ml of water. Test samples were separately prepared to contain 3 ml of the aqueous broth and 1 ml of the dye. The thus-prepared test samples (MR-160 or MR-40) contained 59,760 SU/ml or 14,940 SU/ml of the enzyme, respectively, and 0.05 mM of the dye. The test samples were put into $1.1 \times 10$ cm test tubes which were then positioned in an irradiation chamber equidistant (38 cm) between two 150 W incandescent light bulbs cooled by air fans. The temperature was not maintained constant but allowed to increase gradually, due to the incandescent heat, from an initial temperature of about 24° C. to a maximum of about 37° C. during irradiation. To photooxidize the test samples, the light bulbs were switched on, and a stream of oxygen was slowly fluxed through the test sample for a period of five hours. To prepare the samples for milk-clotting activity assays at the end of the irradiation period, the test samples were diluted to 100 ml with 0.2 M sodium phosphate buffer (pH 5.5). The test sample coded MR-160 was further diluted (1:8 V/V) with 0.2 M sodium phosphate buffer (pH 5.5).

Control samples were prepared by diluting 3 ml of the original enzyme broths to 100 ml with 0.2 M sodium phosphate buffer (pH 5.5). The control coded MR-160 was further diluted (1:8 V/V) with the 0.2 M sodium phosphate buffer (pH 5.5).

Milk-clotting (MC) activities were determined on the diluted test samples and controls using the procedure described in Example 1. The thermal stability of the test samples and controls was determined using the pasteurization procedure (at 66° C. for 10 minutes) described in Example 1. After this heat treatment, the samples were cooled by immersion in an ice-water bath and were assayed for their residual milk-clotting activities and reported as a percentage of the original activity before pasteurization. The data are reported in Table L below.

TABLE L

| Sample | Before Pasteurization % of Original MC Activity | After Pasteurization % Residual Activity |
|---|---|---|
| Control, MR-160 | 100 | 81 |
| Test, MR-160 | 90.5 | 65 |
| Control, MR-40 | 100 | 80.7 |
| Test, MR-40 | 98.9 | 8.7 |

The data in Table L illustrate that dye-sensitized photooxidation is effective to dramatically reduce the heat stability of the thus-treated microbial rennet as compared with the untreated control.

EXAMPLE 9

This example illustrates the effectiveness of dye-sensitized photooxidation used in this invention as a methionnine-oxidizing means.

An aqueous stock solution of microbial rennet was prepared by dissolving 20 mg of purified *Mucor miehei* microbial rennet in 20 ml of distilled water to give a solution having an unadjusted pH of 4.85. Twenty (20) ml of a 0.2 mM methylene blue solution were then added to the stock solution. The thus-prepared solution contained 5000 SU/ml of the rennet and 0.1 mM of the dye. Ten (10) ml aliquots of this solution were photooxidized (30 minutes) as described in Example 8. The milk-clotting activities of the photooxidized samples and an untreated control were determined using the procedure described in Example 1. The thermal stability of the treated samples and untreated control was determined using the pasteurization procedure described in Example 1. The milk-clotting activities were measured after pasteurization and reported as a percentage of the original activity before pasteurization. The data are reported in Table M below.

TABLE M

| Sample | Before Pasteurization % of Original MC Activity | After Pasteurization % Residual MC Activity |
|---|---|---|
| Control | 100 | 93 |
| Test Sample | 84.6 | 37 |

The above data, Table M, illustrate that the photooxidation is effective to dramatically reduce the heat stability of the enzyme as expressed in terms of its milk-clotting activities and as compared with the untreated control.

A portion of the photooxidized sample was further dialyzed (cellulose tubing) against water to remove the dye. The dialyzed sample was then lyophilized. The lyophilized sample and the native purified microbial rennet were subjected to alkaline hydrolysis as described in Example 1, and the hydrolyzed materials were subjected to automatic amino acid analysis. The partial amino acid profiles are given in the following Table N.

TABLE N

| Amino Acid | Quantity (ng) Native | Quantity (ng) Photooxidized |
|---|---|---|
| Methionine sulfoxide | 0 | 151 |
| Aspartic Acid | 2370.4 | 2029.9 |
| Threonine | 45.6 | 37.5 |
| Serine | 406.1 | 406.2 |
| Glutamic Acid | 1455.7 | 1573.9 |
| Proline | 22.7 | 22.3 |
| Glycine | 1621.9 | 1674.5 |
| Alanine | 1567.5 | 1663.8 |
| Valine | 608.2 | 642.3 |
| Methionine | 334.8 | 213.8 |

The above data in Table N illustrate that the dye sensitized photooxidation was effective to oxidize a portion of the methionine residues in the enzyme to methionine sulfoxide.

EXAMPLE 10

This example illustrates the treatment of Mucor microbial rennet using dye-sensitized photooxidation over a broad pH range and a brief contact time.

An aqueous stock solution of microbial rennet was prepared by dissolving 30 mg of purified *Mucor miehei* microbial rennet in 15 ml of distilled water to give a solution containing 20,000 SU/ml. A 0.2 mM solution of methylene blue was prepared by dissolving 74.8 mg of the dye in 1000 ml of water. A 0.2 mM solution of rose bengal was prepared by dissolving 203.5 mg of the dye in 1000 ml of water. Various 0.2 M sodium phosphate buffers were prepared to have pH values between 3.0 and 8.0. Test samples were prepared to contain 1 ml of the enzyme stock solution, 2 ml of one of the dye solutions and 1 ml of water (thus having an initial unadjusted pH of 4.85) or 1 ml of a buffer solution to adjust the pH of the test sample between pH 3.0 and 8.0. The thus-prepared test samples contained 5000 SU/ml of the enzyme and 0.1 mM of the respective dye. Control samples of the enzyme were prepared in a similar manner without buffer or dye using a comparable volume of water for replacement. The samples were then photooxidized as described in Example 8 for a short period of 15 minutes. After irradiation, the samples were each dialyzed (cellophane tubing) against water to remove dye and buffer. The remaining material was then diluted to 50 ml with 0.2 M sodium phosphate buffer (pH 5.5). The milk-clotting activities were determined using the procedure described in Example 1. These results are given in Table O below.

TABLE O

| Treatment pH | % of Original MC Activity Methylene Blue | Rose Bengal |
|---|---|---|
| 3.0 | 85.1 | 73.6 |
| 4.85(H$_2$O) | 79.2 | ND* |
| 5.0 | 87 | 63.8 |
| 5.5 | 88.4 | 57.7 |
| 6.0 | 80.9 | 74.5 |
| 6.5 | 72.2 | 75 |
| 7.0 | 70.4 | 57.1 |
| 7.5 | 49.6 | 37.3 |
| 8.0 | 11.2 | ND* |

*Not determined

A similarly treated control without dye and buffer prepared with 1 ml of the enzyme stock solution and 3 ml of water retained 74% of the original MC activity.

A comparison of the data in the above Table O shows that the microbial rennet can be treated with the dye-sensitized oxidizing means over a broad pH range from 3.0 to 8.0. Preferably the pH is between 3.0 and 7.5.

The thermal stability of each of the treated microbial rennet portions was determined using the pasteurization procedure described in Example 1. The milk-clotting activities were measured after pasteurization and reported as a percentage of the original activity before pasteurization. The data are reported in Table P below.

TABLE P

| Treatment pH | Pasteurization Time (Minutes) at 66° C. | % Residual MC Activity Methylene Blue | Rose Bengal |
|---|---|---|---|
| 3.0 | 0 | 100 | 100 |
|  | 10 | 87 | 82 |
| 4.85(H$_2$O) | 0 | 100 | ND* |
|  | 10 | 48 | ND* |
| 5.0 | 0 | 100 | 100 |
|  | 10 | 69 | 50 |
| 5.5 | 0 | 100 | 100 |
|  | 10 | 63 | 49 |

TABLE P-continued

| Treatment pH | Pasteurization Time (Minutes) at 66° C. | % Residual MC Activity | |
|---|---|---|---|
| | | Methylene Blue | Rose Bengal |
| 6.0 | 0 | 100 | 100 |
| | 10 | 63 | 48 |
| 6.5 | 0 | 100 | 100 |
| | 10 | 60 | 45 |
| 7.0 | 0 | 100 | 100 |
| | 10 | 54 | 42 |
| 7.5 | 0 | 100 | 100 |
| | 10 | 61 | 28 |
| Control(no dye) | 0 | 100 | 100 |
| | 10 | 94 | 85 |

*Not determined

The above data in Table P clearly illustrate that the dye-sensitized photooxidation treatment, even using a brief contact time, is effective to reduce the heat stability of the enzyme even over a broad pH range, preferably between pH 3.0 and 7.5.

What is claimed is:

1. A process for treating a Mucor microbial rennet whereby the original milk-clotting activity thereof is not substantially reduced prior to any subsequent thermal treatment thereof and whereby the thermal stability of the microbial rennet is decreased to about the thermal stability of calf rennet when heated at the same temperature for pasteurizing whey which comprises contacting an aqueous solution thereof at a temperature between about 4° C. and 30° C. and at a pH between about 3.0 and 8.0 and for a time between about 15 minutes and 72 hours with a methionine-oxidizing means that oxidizes at least a portion of the methionine residues in the Mucor microbial rennet to methionine sulfoxide.

2. A process according to claim 1, wherein the microbial rennet is produced from *Mucor miehei*.

3. A process according to claim 1, wherein the microbial rennet is produced from *Mucor pusillus*.

4. A process according to claim 1, wherein the thermal stability of the microbial rennet, expressed in terms of residual milk-clotting activity after thermal treatment, is decreased to at least below about 20 percent of the original activity.

5. A process according to claim 1, wherein the microbial rennet is present in the aqueous solution at a concentration, expressed in terms of milk-clotting activity values, ranging from about 5,000 to 100,000 Soxhlet Units per milliliter.

6. A process according to claim 1, wherein the methionine-oxidizing means is dye-sensitized photooxidation which comprises contacting the aqueous rennet solution with oxygen in the presence of light and a photosensitizer present in a concentration of from about 0.0025 mM to about 1.0 mM.

7. A process according to claim 6, wherein the photosensitizer is methylene blue or rose bengal.

8. A Mucor microbial rennet having substantially decreased thermal stability produced according to the process of claim 1.

9. A process for treating a Mucor microbial rennet whereby the original milk-clotting activity thereof is not substantially reduced prior to any subsequent thermal treatment thereof and whereby the thermal stability of the microbial rennet is decreased to about the thermal stability of calf rennet when heated at the same temperature for pasteurizing whey which comprises contacting an aqueous solution thereof at a temperature between about 4° C. and 30° C. and at a pH between about 3.0 and 8.0 and for a time between about 15 minutes and 72 hours with hydrogen peroxide.

10. A process according to claim 9, wherein the concentration of hydrogen peroxide is between about 1% and 25% on a volume/volume basis based upon the original volume of the aqueous solution.

11. A process according to claim 10, wherein the hydrogen peroxide concentration is between 2% and 10% on a volume/volume basis based upon the original volume of the aqueous solution.

12. A process according to claim 9, wherein the hydrogen peroxide is produced in situ.

13. A process according to claim 12, wherein the hydrogen peroxide is produced in situ with a compound selected from the group consisting of sodium peroxide, calcium peroxide, benzoyl hydroperoxide, a mixture of cumene hydroperoxide and peroxidase, and urea hydrogen peroxide.

14. A process according to claim 13, wherein the compound is calcium peroxide.

15. A process according to claim 9, wherein residual hydrogen peroxide in the solution is substantially destroyed.

16. A process according to claim 15, wherein the hydrogen peroxide is substantially destroyed with a material selected from the group consisting of catalase, peroxidase and ascorbic acid.

17. A process according to claim 16, wherein the catalase is beef liver catalase and the peroxidase is horseradish peroxidase.

18. A Mucor microbial rennet having substantially reduced thermal stability produced according to the process of claim 9.

* * * * *